United States Patent [19]

Miki et al.

[11] Patent Number: 5,824,872
[45] Date of Patent: Oct. 20, 1998

[54] A CONSTITUTIVE PROMOTER FROM TOBACCO

[76] Inventors: Brian Miki, 1876 Dorset Dr., Ottawa, Ontario, Canada, K1H 5V1; Jiro Hattori, 763 Halstead St., Ottawa, Ontario, Canada, K1G 1M5; Pierre Fobert, 878 Kingsmere Blvd., Saskatoon, Saskatchewan, Canada, S7J 4J7; Venkatran N. Iyer, 139 Iona St., Ottawa, Ontario, Canada, K1Y 3M2

[21] Appl. No.: 593,121

[22] Filed: Feb. 1, 1996

[51] Int. Cl.$^6$ .............................. A01H 5/00; C12N 15/82; C12N 15/63; C07H 21/04

[52] U.S. Cl. ..................... 800/205; 435/69.1; 435/320.1; 536/24.1

[58] Field of Search ................................ 435/69.1, 320.1; 536/24.1; 800/205

[56] References Cited

PUBLICATIONS

Kim et al. A 20 nucleotide upstream element is essential for the nopaline synthase (nos) promoter activity. Plant Molecular Biology 24:105–117, 1994.
Benfey et al. Tissue–specific expression from CaMV 35S enhancer subdomains in early stages of plant development. The EMBO Journal. 9(6):1677–1784, 1990.
Lam et al. A metal–dependent DNA–binding protein interacts with a constitutive element of a light–responsive promoter. The Plant Cell. 2:857–866, 1990.
Forbert, Pierre R. "Characterization of Chromosomal Sites of T–DNA Integration By Activation of a Promoterless β–Glucuronidase (GUS) Gene Linked to the T–DNA Right Border Repeat" (1992), Carleton University, Department of Biology, Ottawa.
An, et al., "Organ–Specific and Developmental Regulation of the Nopaline Synthase Promoter in Transgenic Tobacco Plants," *Plant Physiol.*, vol. 88:547–552, 1988.
Bevan, et al., "A Chimaeric Antibiotic Resistance Gene as a Selectable Marker for Plant Cell Transformation," *Nature*, vol. 304:184–187, Jul., 1983.
Callis, et al., "Ubiquitin Extension Proteins of *Arabidopsis thaliana*," *The Journal of Biological Chemistry*, vol. 265:12486–12493.
Cornejo, et al., "Activity of a Maize Ubiquitin Promoter in Transgenic Rice," *Plant Molecular Biology*, vol. 23:567–581, 1993.
Fraley, et al., "Expression of Bacterial Genes in Plant Cells," *Proc. Natl. Acad. Sci. USA*, vol. 80:4803–4807, Aug., 1983.
Guilley, et al., "Transcription of Cauliflower Mosaic Virus DNA: Detection of Promoter Sequences, and Characterization of transcripts," *Cell*, vol. 30:763–773, Oct., 1982.
Holtorf, et al., "Comparison of Different Constitutive and Inducible Promoters for the Overexpression of Transgenes in *Arabidopsis thaliana*," *Plant Molecular Biology*, vol. 29:637–646, 1995.
Kay, et al., "Duplication of CaMV 35S Promoter Sequences Creates a Strong Enhancer for Plant Genes," *Science*, vol. 236:1299–1302, Jun., 1987.
Mandel, et al., "Definition of a Constitutive Gene Expression in Plants: the Translation Initiation Factor 4A Gene as a Model," *Plant Molecular Biology*, vol. 29:995–1004, 1995.
Ni, et al., "Strength and Tissue Specificity of Chimeric Promoters Derived from the Octopine and Mannopine Synthase Genes," *The Plant Journal*, vol. 7(4):661–676, 1995.
Odell, et al., "Identification of DNA Sequences Required for Activity of the Cauliflower Mosaic Virus 35S Promoter," *Nature*, vol. 313:810–812, Feb., 1985.
Otten, I., et al., "Mendelian Transmission of Genes Introduced into Plants by the Ti Plasmids of *Agrobacterium tumefaciens*," *Mol Gen Genet*, vol. 183:209–213, 1981.
Sanger, et al., "Characteristics of a Strong Promoter From Figwort Mosaic Virus: Comparison with the Analogous 35S Promoter From Cauliflower Mosaic Virus and the Regulated Mannopine Synthase Promoter," *Plant Molecular Biology*, vol. 14:433–443, 1990.
Shah, et al., "Engineering Herbicide Tolerance in Transgenic Plants," *Science*, vol. 233:478–481, Jul., 1986.
Xu, et al., "Rice Triosephosphate Isomerase Gene 5' Sequence Directs β–Glucuronidase Activity in Transgenic Tobacco but Requires an Intron for Expression in Rice," *Plant Physiol.*, vol. 106:459–467, 1994.
Zhang, et al., "Analysis of Rice ActI 5' Region Activity in Transgenic Rice Plants," *The Plant Cell*, vol. 3:1155–1165., Nov., 1991.
"Detection of gene regulatory signals in plants revealed by T–DNA–mediated fusions," Fobert et al. *Plant Molecular Biology*, 17:837–851, 1991.

*Primary Examiner*—Douglas W. Robinson
*Assistant Examiner*—Thanda Wai
*Attorney, Agent, or Firm*—Testa, Hurwitz & Thibeault, LLP

[57] ABSTRACT

T-DNA tagging with a promoterless β-glucuronidase (GUS) gene generated a transgenic *Nicotiana tabacum* plant that expressed GUS activity constitutively. The gene fusion has been cloned and sequenced. It has been re-inserted into *N. tabacum* by Agrobacterium-mediated transformation. The *N. tabacum* DNA upstream from the GUS gene was approximately 2 kb in length and showed no homology to known sequences. This DNA, which contains a constitutive promoter, is useful in controlling the expression of exogenous genes in transgenic plants of diverse plant species.

5 Claims, 6 Drawing Sheets

T1275

```
TCTAGACTTA CAGAAAGTCT CTAACACGTG AGGGAATGAT CCCTTTCCTT ACCTCCCTGT
AGAGATATTG GCTTTTCAAC AACTAGTACA TAAATATGCG ACTTTGACCG TGTATCCCCA
GTCAAAAGGG AACTTCACCC TCCTAGTTCT TTATTTCCAA CATACATGGG GAGTAATGCT
AAATTTACAT AGAAGAATAA TAAAATGAAC TGTAACTAAT GATGTACTGT TCCAAAGAGA
TGAGGACGTC AACATATTTA TTCCTTCAGC CCTTTTCAGA ATAATACCAT AAGTAGAAGA
AATGGCACAT AAAATGAAGT CCTCGGCAAG TCAAATGTAA ATCTGAACCC ACCCAGCTAA
CCCAGTGAAC TCAACTTTCC TGGATAGATC AGCACTCCTT CATGACATTG CATGCCTTCT
CTTTAAAGAG CCGCTTGATC TCTGAAAACC AAATGAATCT CCACAGAGAG ATTTCGAGCT
CCATGAGACG CCTTTTGGTT CTTGATTTAC TAAACCTATA AAAATGAAAG GAAGTAGGAC
AACTGCATTT TGCCGCTTAA GATGCTTCGG CGCTTTGTGA ATTTTAAGTC ATGAGAAAGT
ACAATGTTGG AATCTCACAT TAGAACAATG TATTTGTAAT AACCTAGGAA AGCAAAGCTA
GAAGGGAGGT GCAGCTAAAT CTTCTTCTAC CTTGTTATCC TTGCATTTCT TGAGGAGGAG
GAACTGTCCT CGCAGGTGCA AAATCTGCAG TCGCCCAAAA GGATATTCAG AAGTATATTA
CAACATGTTT AATGGTTAAC CAAGTGAAAG ATCAAAATAG TCATTAGAAC AAAATGCGTG
CTCAGAGCGT ATCTACTAGT TCATCAACCC AGTACACATC TCTGAATTTC ATCTCTTGCC
GTTGAACTAA GTCAATTGGT CAAAGACGCA TAACATGAGA GACACTCATA AAACGGCTGA
ATAACATGCA GAAGACGTCA TGCGCCTTAG GTCTCATTAT GCATGAGATT ATTAGTTATA
TGCTCCTTCA GTTTGACTAG AAATGAAAAA TCAGTTAAGC CTGTAACGAA ATGATAACCT
GCTTCAAGAA GATTAGACTA TTTTTCATAA AATATGCAGT GCCGTGAAAT AGATACTTAA
TCTTAGGCAG GAAAAATCTT CTATTGGGCC ATAATAAGAA CTACCAATTA GAAAGGAGGT
AGAAAGCTCC GATACTGTTA TGAAGGCCAT TCTAAGTGCT GATGTGAATT TCCCAATACA
AAATGACAAC AAAAACAAAA GCCTCAATCC TAAGCTAGTT GGGGTCGCTA TATAAATCCT
CGACATCCAT TTAACTCCAC TTGGACTCCT TTCTTTCCAA TATTTTAATA TTGTTAGATT
AATCATAAAA TTGCTTAGCT TTCTACTGGC ACTTAACCTA CTGCAACCCT CCTCTTCTGG
GATTCCAACA CAAACAACTA AGAGGAATTT GAAAAAAAGA AAGCAAATGT GAGAAGAGAC
AAAATGTACA ATGATACCTC TTCTTGCAGC AAAGGAGGCA GGTCTCTGC TGAGACAAGG
TTCTCTATTT CCTGCAAGAC CTTCGTATCT TTTATTCGAG ACCATGTATG TGGAGGTAAC
GCCAGCAATA GTGCTGTCAG CACATCGTTG CTTGCAGGGG ATCTTCTGCA AGCATCTCTA
TTTCCTGAAG GTCTAACCTC GAAGATTTAA GATTTAATTA CGTTATAAT TACAAAATTG
ATTCTAGTAT CTTTAATTTA ATGCTTATAC ATTATTAATT AATTTAGTAC TTTCAATTTG
TTTTCAGAAA TTATTTTACT ATTTTTTATA AAATAAAAGG GAGAAAATGG CTATTTAAAT
ACTAGCCTAT TTTATTTCAA TTTTAGCTTA AAATCAGCCC CAATTAGCCC CAATTTCAAA
TTCAAATGGT CCAGCCCAAT TCCTAAATAA CCCACCCCTA ACCCGCCCGG TTTCCCCTTT
TGATCCAGGC CGTTGATCAT TTTGATCAAC GCCCAGAATT TCCCCTTTTC CTTTTTTAAT
TCCCAAACAC CCCTAACTCT ATCCCATTTC TCACCAACCG CCACATATGA ATCCTCTTAT
CTCTCAAACT CTCTCGAACC TTCCCCTAAC CCTAGCAGCC TCTCATCATC CTCACCTCAA
AACCCACCGG AATACATGGC TTCTCAAGCC GTGGAAACCT TATACTCACC TCCCTTTGCT
CTTACAGTAC TCGGCCGTCG ACCGCGGTAC CCGGG
```

FIGURE 5

A CONSTITUTIVE PROMOTER FROM TOBACCO

FIELD OF INVENTION

The present invention relates to a constitutive promoter identified from *Nicotiana tabacum* (tobacco). This invention further relates to the use of said constitutive promoter to control the expression of exogenous genes in transgenic plants of diverse plant species.

BACKGROUND OF THE INVENTION

Bacteria from the genus Agrobacterium have the ability to transfer specific segments of DNA (T-DNA) to plant cells, where they stably integrate into the nuclear chromosomes. Analyses of plants harbouring the T-DNA have revealed that this genetic element may be integrated at numerous locations, and can occasionally be found within genes. One strategy which has been exploited to identify integration events within genes is to transform plant cells with specially designed T-DNA vectors which contain a reporter gene, devoid of cis-acting transcriptional and translational expression signals (i.e. promoterless), located at the end of the T-DNA. Upon integration, the initiation codon of the promoterless gene (reporter gene) will be juxtaposed to plant sequences. The consequence of T-DNA insertion adjacent to, and downstream of, gene promoter elements may be the activation of reporter gene expression. The resulting hybrid genes, referred to as T-DNA-mediated gene fusions, consist of unknown and thus un-characterized plant promoters residing at their natural location within the chromosome, and the coding sequence of a marker gene located on the inserted T-DNA (Fobert et al., 1991, Plant Mol. Biol. 17, 837–851).

It has generally been assumed that activation of promoterless or enhancerless marker genes result from T-DNA insertions within or immediately adjacent to genes. The recent isolation of several T-DNA insertional mutants (Koncz et al., 1992, *Plant Mol. Biol.* 20, 963–976; reviewed in Feldmann, 1991, *Plant J.* 1, 71–82; Van Lijsebettens et al., 1991, *Plant Sci.* 80, 27–37; Walden et al., 1991, *Plant J.* 1:281–288; Yanofsky et al., 1990, *Nature* 346, 35–39), shows that this is the case for at least some insertions. However, other possibilities exist. One of these possibilities is that integration of the T-DNA activates silent regulatory sequences that are not associated with genes. Lindsey et al. (1993, *Transgenic Res.* 2, 33–47) referred to such sequences as "pseudo-promoters" and suggested that they may be responsible for activating marker genes in some transgenic lines. Fobert et al. (1994, *Plant J.* 6, 567–577) have cloned such sequences and have referred to these as "cryptic promoters".

SUMMARY OF THE INVENTION

The present invention is directed to a constitutive promoter identified from *Nicotiana tabacum* (tobacco).

The transgenic tobacco plant, T1275, contained a 4.2 kb EcoRI/XbaI fragment containing the 2.2 kb promoterless GUS-nos gene and 2.0 kb of 5' flanking tobacco DNA. This 5' flanking DNA showed no homology to known sequences. Expression of the cloned fragment in transgenic tobacco is apparent on cultured leaf discs and in the early stages of shoot development.

Thus according to the present invention there is provided a constitutive promoter from tobacco. The present invention is further directed to a constitutive promoter having a DNA sequence, substantially homologous to SEQ ID NO:1.

This invention also relates to a chimeric gene construct comprising: a constitutive promoter, having a DNA sequence substantially homologous to SEQ ID NO:1, and a gene encoding a protein, for which constitutive expression is desired.

This invention further relates to a cloning vector containing said chimeric gene construct.

This invention also includes a plant cell which has been transformed with said cloning vector.

This invention further relates to a transgenic plant containing a constitutive promoter, having a DNA sequence substantially homologous to SEQ ID NO:1, operatively linked to a gene encoding a protein.

Also included in the present invention is a method of conferring constitutive expression on a gene in a plant, comprising: operatively linking an exogenous gene, for which constitutive expression is desired, with a constitutive promoter, to produce a chimeric gene construct and introducing the chimeric gene construct into a plant capable of expressing the chimeric gene construct.

BRIEF DESCRIPTION OF THE DRAWINGS

These and other features of the invention will become more apparent from the following description in which reference is made to the appended drawings wherein:

FIG. 5 shows the nucleotide sequence (SEQ ID NO:1) for the Xba I—Sal I fragment of pT1275.

DESCRIPTION OF PREFERRED EMBODIMENT

Figure 1A:
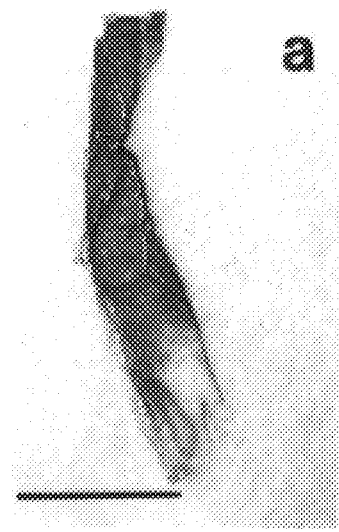
FIG. 1 shows the constitutive expression of GUS in all tissues of plant T1275, including leaf segments (a), stem cross-sections (b), roots (c), flower cross-sections (d), ovary cross-sections (e), immature embryos (f), mature embryos (g), and seed cross-sections (h).
Figure 1B:
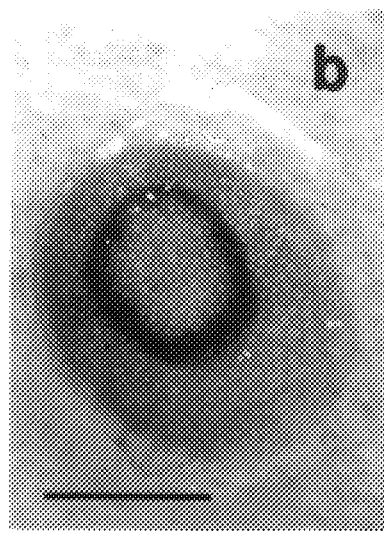
Figure 1C:
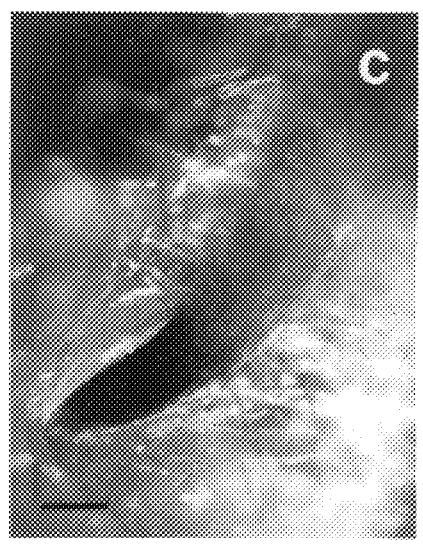
Figure 1D:
Figure 1E:
Figure 1F:
Figure 1G:
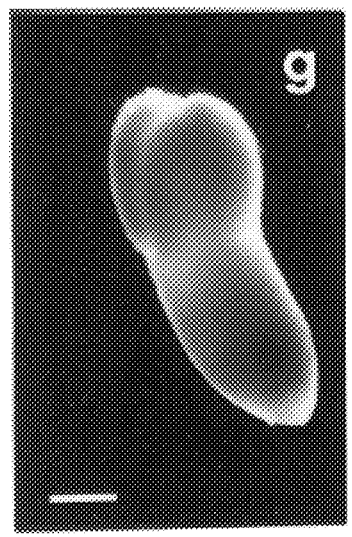
Figure 1H:
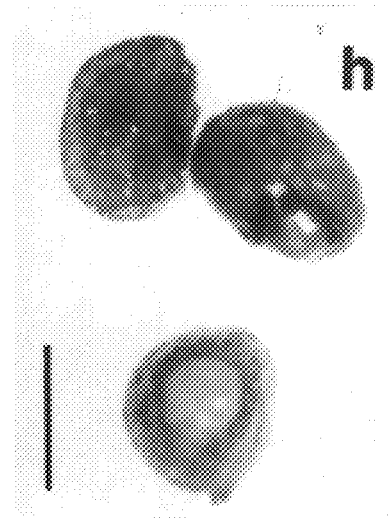

The present invention relates to plant gene promoters. Specifically this invention relates to a constitutive promoter, identified by T-DNA tagging with a promoterless β-glucuronidase gene (GUS) to generate a transgenic *N. tabacum* plant that expresses GUS activity constitutively.

In the context of this disclosure, the term "promoter" or "promoter region" refers to a sequence of DNA, usually upstream (5') to the coding sequence of a structural gene, which controls the expression of the coding region by providing the recognition for RNA polymerase and/or other factors required for transcription to start at the correct site.

There are generally two types of promoters, inducible and constitutive promoters. An inducible promoter is a promoter that is capable of directly or indirectly activating transcription of one or more DNA sequences or genes in response to an inducer. In the absence of an inducer the DNA sequences or genes will not be transcribed. Typically the protein factor, that binds specifically to an inducible promoter to activate transcription, is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible promoter may be exposed to an inducer by externally applying the inducer to the cell or plant such as by spraying, watering, heating or similar methods.

The present invention is directed to a constitutive promoter which directs the expression of a gene, constitutively. Specifically, the present invention is directed to a constitutive promoter isolated from *N. tabacum*. A constitutive promoter directs the expression of a gene throughout the various parts of a plant and continuously throughout plant development. Examples of known constitutive promoters include those associated with the CaMV 35S transcript and Agrobacterium Ti plasmid nopaline synthase gene (Sanders et al. 1987, *Nucleic Acids Res.* 15, 1543–1558). The constitutive promoter of the present invention demonstrated levels of expression greater than that using the CaMV 35S promoter.

The term "constitutive" as used herein does not necessarily indicate that a gene is expressed at the same level in all cell types, but that the gene is expressed in a wide range of cell types, although some variation in abundance is often observed.

The present invention is further directed to a chimeric gene construct containing a gene of interest operatively linked to the constitutive promoter of the present invention. Any exogenous gene can be used and manipulated according to the present invention to result in the constitutive expression of said exogenous gene.

The chimeric gene construct of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon.

Examples of suitable 3' regions are the 3' transcribed non-translated regions containing a polyadenylation signal of Agrobacterium tumor inducing (Ti) plasmid genes, such as the nopaline synthase (Nos gene) and plant genes such as the soybean storage protein genes and the small subunit of the ribulose-1, 5-bisphosphate carboxylase (ssRUBISCO) gene. The 3' untranslated region from the structural gene of the present construct can therefore be used to construct chimeric genes for expression in plants.

The chimeric gene construct of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the promoter selected to express the gene, and can be specifically modified so as to increase translation of the mRNA.

To aid in identification of transformed plant cells, the constructs of this invention may be further manipulated to include plant selectable markers. Useful selectable markers include enzymes which provide for resistance to an antibiotic such as gentamycin, hygromycin, kanamycin, and the like. Similarly, enzymes providing for production of a compound identifiable by colour change such as GUS (β-glucuronidase), or luminescence, such as luciferase are useful.

Also considered part of this invention are transgenic plants containing the chimeric gene construct of the present invention. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology,* Academy Press, New York VIII, pp. 421–463 (1988); and Geierson and Corey, *Plant Molecular Biology,* 2d Ed. (1988). The present invention further includes a suitable vector comprising the chimeric gene construct.

When specific sequences are referred to in the present invention, it is understood that these sequences include within their scope sequences that are "substantially homologous" to said specific sequences. Sequences are "substantially homologous" when at least about 80%, preferably at least about 90% and most preferably at least about 95% of the nucleotides match over a defined length of the molecule. Sequences that are "substantially homologous" include any substitution, deletion, or addition within the sequence. DNA sequences that are substantially homologous can be identified in Southern hybridization experiments, for example under stringent hybridization conditions (see Maniatis et al., in Molecular Cloning (A Laboratory Manual), Cold Spring Harbor Laboratory (1982) p 387 to 389).

The specific sequences, referred to in the present invention, also include sequences which are "functionally equivalent" to said specific sequences. In the present invention functionally equivalent sequences refer to sequences which although not identical to the specific sequences provide the same or substantially the same function. DNA sequences that are functionally equivalent include any substitution, deletion or addition within the sequence. With reference to the present invention functionally equivalent sequences will direct the expression of an exogenous gene constitutively.

While this invention is described in detail with particular reference to preferred embodiments thereof, said embodiments are offered to illustrate but not limit the invention.

EXAMPLES

Characterization of a Constitutive Promoter—GUS Fusion

Transfer of binary constructs to Agrobacterium and leaf disc transformation of *N. tabacum* SR1 were performed as described by Fobert et al. (1991, *Plant Mol. Biol.* 17, 837–851). Plant tissue was maintained on 100 µg/ml kanamycin sulfate (Sigma) throughout in vitro culture.

From the transgenic plants produced, one of these, T1275, was chosen for detailed study because of its high level and constitutive expression of GUS.

Fluorogenic and histological GUS assays were performed according to Jefferson (*Plant Mol. Biol. Rep.*, 1987, 5, 387–405), as modified by Fobert et al. (*Plant Mol. Biol.*, 1991, 17, 837–851). For initial screening, leaves were harvested from in vitro grown plantlets. Later nine different tissues: leaf (L), stem (S), root (R), anther (A), petal (P), ovary (O), sepal (Se), seeds 10 days post anthesis (S1) and seeds 20 days post-anthesis (S2), were collected from plants grown in the greenhouse and analyzed. For detailed, quantitative analysis of GUS activity, leaf, stem and root tissues were collected from kanamycin resistant F1 progeny grown in vitro. Floral tissues were harvested at developmental stages 8–10 (Koltunow et al., 1990, *Plant Cell* 2, 1201–1224) from the original transgenic plants. Flowers were also tagged and developing seeds were collected from capsules at 10 and 20 dpa. In all cases, tissue was weighed, immediately frozen in liquid nitrogen, and stored at −80° C.

Tissues analyzed by histological assay were at the same developmental stages as those listed above. Different handcut sections were analyzed for each organ. For each plant, histological assays were performed on at least two different occasions to ensure reproducibility. Except for floral organs, all tissues were assayed in phosphate buffer according to Jefferson (1987, *Plant Mol. Biol. Rep. 5, 387–405*), with 1 mM X-Gluc (Sigma) as substrate. Flowers were assayed in the same buffer containing 20% (v/v) methanol (Kosugi et al., 1990, *Plant Sci.* 70, 133–140).

GUS activity in plant T1275 was found in all tissues. FIG. 1 shows the constitutive expression of GUS by histochemical staining with X-Gluc of T1275, including leaf (a), stem (b), root (c), flower (d), ovary (e), embryos (f and g), and seed (h).

Figure 2:
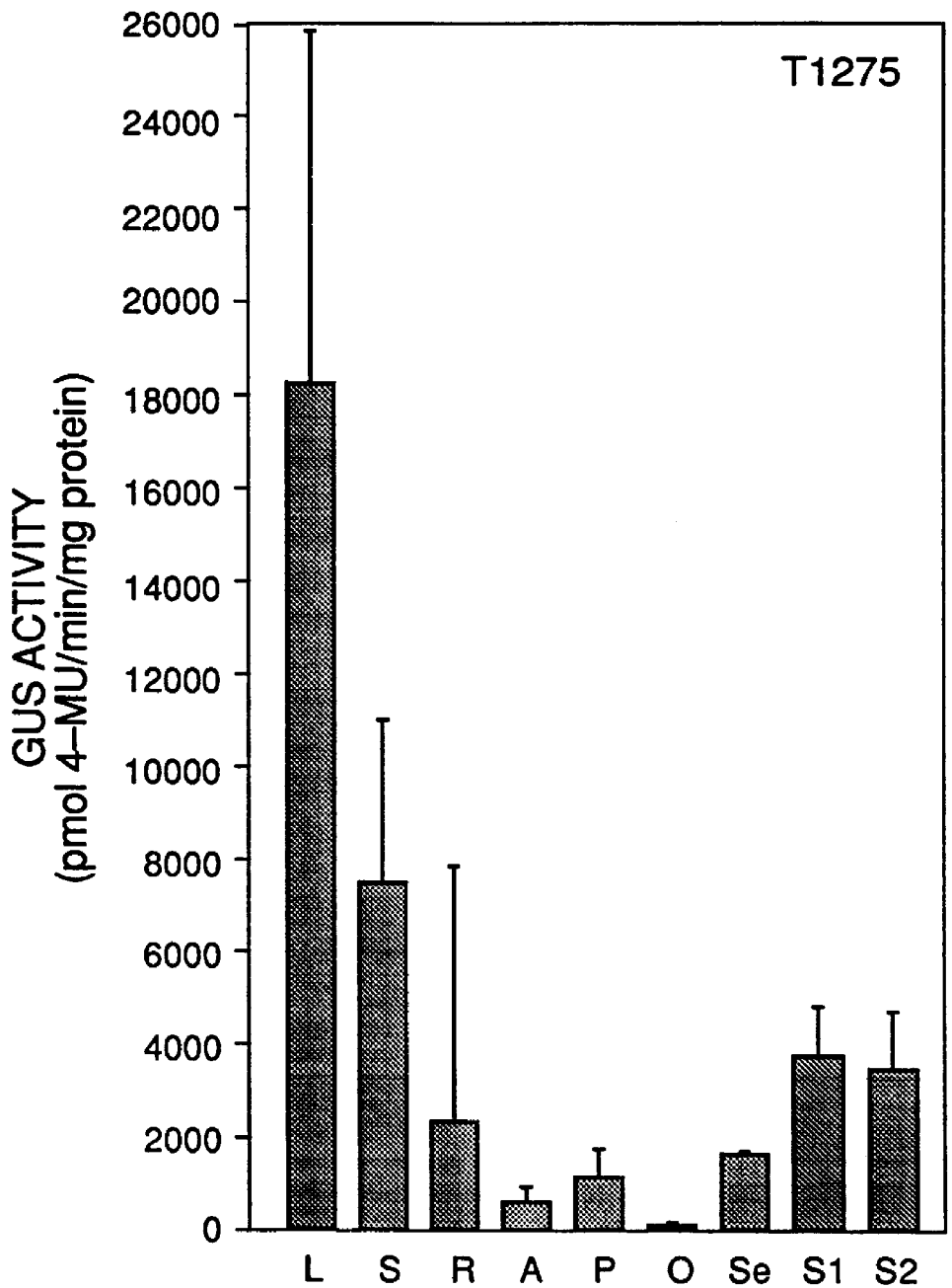
FIG. 2 shows the GUS fluorogenic activity, which reveals that the level of GUS expression in T1275 is comparable to levels in plants expressing CaMV 35S—GUS—nos genes in leaf tissues.

Constitutive GUS expression was confirmed with the more sensitive fluorogenic assay of plant tissue from transformed plant T1275. These results are shown in FIG. 2. GUS expression was evident in all tissue types including leaf (L), stem (S), root (R), anther (A), pistil (P), ovary (O), sepal (Se), seeds at 10 dpa (S1) and 20 dpa (S2). Furthermore, the level of GUS expression is comparable to the level of expression in transformed plants containing the constitutive promoter CaMV 35S in a GUS—nos fusion. As reported by Fobert et al. (1991, Plant Molecular Biology, 17:837–851) GUS activity in transformed plants containing pBI121 (Clontech), which contains a CaMV 35S—GUS—nos chimeric gene, was as high as 18,770±2450 (pmole MU per minute per mg protein).

Genetic Analysis of Transgenic Plant T1275

The T-DNA contains a kanamycin resistance gene. Seeds from self-pollinated transgenic plants were surface-sterilized in 70% ethanol for 1 min and in undiluted Javex bleach (6% sodium hypochloride) for 25 min. Seeds were then washed several times with sterile distilled water, dried under laminar flow, and placed in Petri dishes containing MSO medium supplemented with 100 µg/ml kanamycin as described in Miki et al. (1993, Methods in Plant Molecular Biology and Biotechnology, Eds., B. R. Glick and J. E. Tompson, CRC Press, Boca Raton, 67–88). At least 90 plantlets were counted for each transformant. The number of green (kanamycin-resistant) and bleached (kanamycin-sensitive) plantlets were counted after 4–6 weeks, and analyzed using the Chi$^2$ test at a significance level of P<0.05.

The genetic analysis results are shown below in Table 1, which demonstrates that the T-DNA loci segregated as a single locus of insertion.

TABLE 1

Genetic Analysis of Transgenic Plant T1275

| No. of Progeny Km$^r$ | No. of Progeny Km$^s$ | Observed Ratio | Expected Ratio | Chi$^2$ |
|---|---|---|---|---|
| 262 | 88 | 3:1* | 3:1 | 0 |

*Consistent with a single dominant gene

Southern Blot Analysis

The T-DNA in the transgenic plant T1275 was analyzed using either a GUS gene coding region probe or a nptII gene coding region probe.

Figure 3:
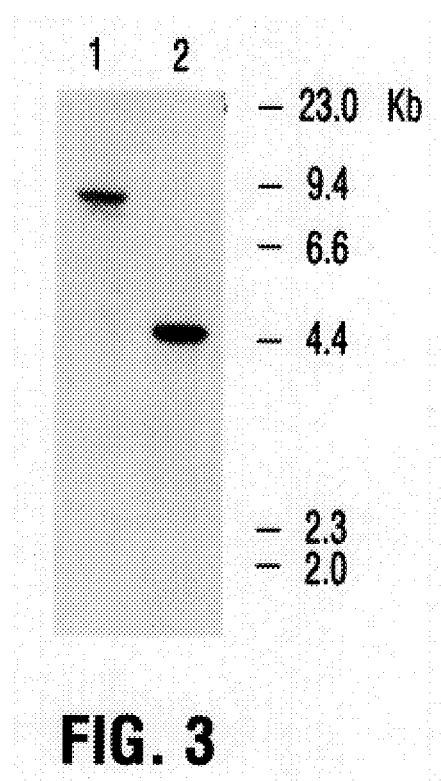
FIG. 3 is the Southern blot analysis of Eco RI digested T1275 DNA with a GUS gene coding region probe (lane 1) and a nptII gene coding region probe (lane 2).

Genomic DNA was isolated from freeze-dried leaves using the protocol of Sanders et al. (1987, *Nucleic Acid Res.* 15, 1543–1558). Ten micrograms of T1275 DNA was digested for several hours with EcoRI using the appropriate manufacturer-supplied buffer supplemented with 2.5 mM spermidine. After electrophoresis through a 0.8% TAE agarose gel, Southern blot analysis was conducted using standard protocols. As the T-DNA from the construct containing the constitutive promoter—GUS—nos construct contains only a single Eco RI recognition site the hybridizing fragments are composed of both T-DNA and flanking tobacco DNA sequences. The length of the fragment will vary depending on the location of the nearest Eco RI site. Using the GUS gene as a probe (FIG. 3—lane 1), the fragment to the nearest Eco RI site in the plant DNA will be detected. With T1275, one such fragment was located. Using the nptII coding region as a probe (FIG. 3—lane 2), which hybridizes to sequences on the opposite side of the Eco RI site, again only one hybridization band was evident. As can also be seen in FIG. 3, no major rearrangements occurred.

Cloning and Analysis of the Constitutive Promoter—GUS Fusion

Figure 4:
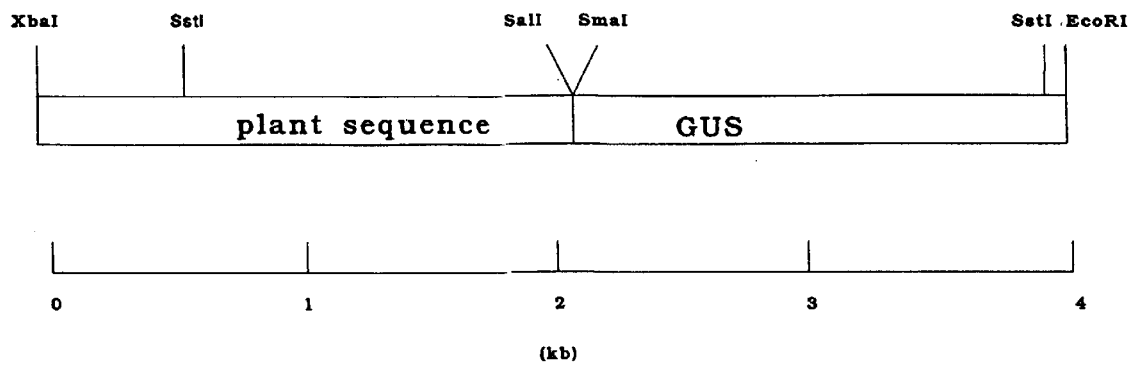
FIG. 4 shows the cloned GUS gene fusion pT1275.

Genomic DNA was isolated from leaves according to Hattori et al. (1987, *Anal. Biochem.* 165, 70–74). Ten µg of T1275 total DNA was digested with EcoRI and XbaI according to the manufacturer's instructions. The digested DNA was size-fractionated on a 0.7% agarose gel. The DNA fragments of about 4 to 6 kb were isolated from the gel using the Elu-Quick kit (Schleicher and Schuell) and ligated to lambdaGEM-2 arms previously digested with EcoRI and XbaI and phosphatase-treated. About 40,000 plaques were transferred to a nylon membrane (Hybond, Amersham) and screened with the $^{32}$P-labelled 2 kb GUS insert isolated form pBI121, essentially as described in Rutledge et al. (1991, *Mol. Gen Genet.* 229, 31–40). The positive clones were isolated. The XbaI-EcoRI fragment (FIG. 4) was isolated from the lambda phage and cloned into pTZ19R previously digested with XbaI and EcoRI and treated with intestinal calf phosphatase.

The 4.2 kb fragment containing about 2.2 kb of the T1275 promoter activity fused to the GUS gene and the nos 3' was isolated by digesting pTZ-T1275 with HindIII and EcoRI. The isolated fragment was ligated into the pRD400 vector (Datla et al., 1992, *Gene,* 211:383–384) previously digested with HindIII and EcoRI and treated with calf intestinal phosphatase. Transfer of the binary vector to *Agrobacterium tumefaciens* and leaf disc transformation of *N. tabacum* SR1 were performed as described above. Histochemical analysis of GUS activity revealed staining of callus tissue after transformation and prior to shoot organogenesis and staining of hoots subsequently. Staining was comparable for shoots transformed with a vector in which the T1275 promoter was replaced with the 3 kb 35S promoter from pBI121.

All scientific publications and patent documents are incorporated herein by reference.

The present invention has been described with regard to preferred embodiments. However, it will be obvious to persons skilled in the art that a number of variations and modifications can be made without departing from the scope of the invention as described in the following claims.

What is claimed is:

1. An isolated constitutive promoter from tobacco that directs expression in at least ovary, flower, immature embryo, mature embryo, seed, stem, leaf and root tissues, wherein said promoter comprises the nucleotide sequence of SEQ ID NO:1.

2. A chimeric gene construct comprising a gene, for which constitutive expression is desired, and a constitutive promoter from tobacco that directs the expression of said gene in at least ovary, flower, immature embryo, mature embryo, seed, stem, leaf and root tissues, wherein said constitutive promoter comprises the nucleotide sequence of SEQ ID NO:1.

3. A vector comprising the chimeric gene construct of claim 2 wherein said constitutive promoter comprises the nucleotide sequence of SEQ ID NO:1.

4. A method of conferring constitutive expression of a gene in a plant, comprising:

operatively linking a gene, for which constitutive expression is desired, with a constitutive promoter from tobacco that directs the expression of said gene in at least ovary, flower, immature embryo, mature embryo, seed, stem, leaf and root tissues, to produce a chimeric gene construct and introducing the chimeric gene construct into a plant capable of expressing the chimeric gene construct, wherein said constitutive promoter comprises the nucleotide sequence of SEQ ID NO:1.

5. A transgenic plant containing the chimeric gene construct of claim 2, wherein said constitutive promoter comprises the nucleotide sequence of SEQ ID NO:1.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 2255 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 1:

```
TCTAGACTTA  CAGAAAGTCT  CTAACACGTG  AGGGAATGAT  CCCTTTCCTT  ACCTCCCTGT      60
AGAGATATTG  GCTTTTCAAC  AACTAGTACA  TAAATATGCG  ACTTTGACCG  TGTATCCCCA     120
GTCAAAGGG   AACTTCACCC  TCCTAGTTCT  TTATTTCCAA  CATACATGGG  GAGTAATGCT     180
AAATTTACAT  AGAAGAATAA  TAAAATGAAC  TGTAACTAAT  GATGTACTGT  TCCAAAGAGA     240
TGAGGACGTC  AACATATTTA  TTCCTTCAGC  CCTTTTCAGA  ATAATACCAT  AAGTAGAAGA     300
AATGGCACAT  AAAATGAAGT  CCTCGGCAAG  TCAAATGTAA  ATCTGAACCC  ACCCAGCTAA     360
CCCAGTGAAC  TCAACTTTCC  TGGATAGATC  AGCACTCCTT  CATGACATTG  CATGCCTTCT     420
CTTTAAAGAG  CCGCTTGATC  TCTGAAAACC  AAATGAATCT  CCACAGAGAG  ATTTCGAGCT     480
CCATGAGACG  CCTTTTGGTT  CTTGATTTAC  TAAACCTATA  AAAATGAAAG  GAAGTAGGAC     540
AACTGCATTT  TGCCGCTTAA  GATGCTTCGG  CGCTTTGTGA  ATTTAAGTC   ATGAGAAAGT     600
ACAATGTTGG  AATCTCACAT  TAGAACAATG  TATTTGTAAT  AACCTAGGAA  AGCAAAGCTA     660
GAAGGGAGGT  GCAGCTAAAT  CTTCTTCTAC  CTTGTTATCC  TTGCATTTCT  TGAGGAGGAG     720
GAACTGTCCT  CGCAGGTGCA  AAATCTGCAG  TCGCCCAAAA  GGATATTCAG  AAGTATATTA     780
CAACATGTTT  AATGGTTAAC  CAAGTGAAAG  ATCAAAATAG  TCATTAGAAC  AAAATGCGTG     840
CTCAGAGCGT  ATCTACTAGT  TCATCAACCC  AGTACACATC  TCTGAATTTC  ATCTCTTGCC     900
GTTGAACTAA  GTCAATTGGT  CAAAGACGCA  TAACATGAGA  GACACTCATA  AAACGGCTGA     960
ATAACATGCA  GAAGACGTCA  TGCGCCTTAG  GTCTCATTAT  GCATGAGATT  ATTAGTTATA    1020
TGCTCCTTCA  GTTTGACTAG  AAATGAAAAA  TCAGTTAAGC  CTGTAACGAA  ATGATAACCT    1080
GCTTCAAGAA  GATTAGACTA  TTTTTCATAA  AATATGCAGT  GCCGTGAAAT  AGATACTTAA    1140
TCTTAGGCAG  GAAAAATCTT  CTATTGGGCC  ATAATAAGAA  CTACCAATTA  GAAAGGAGGT    1200
AGAAAGCTCC  GATACTGTTA  TGAAGGCCAT  TCTAAGTGCT  GATGTGAATT  TCCCAATACA    1260
AAATGACAAC  AAAAACAAAA  GCCTCAATCC  TAAGCTAGTT  GGGGTCGCTA  TATAAATCCT    1320
CGACATCCAT  TTAACTCCAC  TTGGACTCCT  TTCTTTCCAA  TATTTTAATA  TTGTTAGATT    1380
AATCATAAAA  TTGCTTAGCT  TTCTACTGGC  ACTTAACCTA  CTGCAACCCT  CCTCTTCTGG    1440
GATTCCAACA  CAAACAACTA  AGAGGAATTT  GAAAAAAAGA  AAGCAAATGT  GAGAAGAGAC    1500
AAAATGTACA  ATGATACCTC  TTCTTGCAGC  AAAGGAGGCA  GGTTCTCTGC  TGAGACAAGG    1560
TTCTCTATTT  CCTGCAAGAC  CTTCGTATCT  TTTATTCGAG  ACCATGTATG  TGGAGGTAAC    1620
GCCAGCAATA  GTGCTGTCAG  CACATCGTTG  CTTGCAGGGG  ATCTTCTGCA  AGCATCTCTA    1680
```

-continued

| | | | | | | |
|---|---|---|---|---|---|---|
| TTTCCTGAAG | GTCTAACCTC | GAAGATTTAA | GATTTAATTA | CGTTTATAAT | TACAAAATTG | 1740 |
| ATTCTAGTAT | CTTTAATTTA | ATGCTTATAC | ATTATTAATT | AATTAGTAC | TTTCAATTTG | 1800 |
| TTTTCAGAAA | TTATTTTACT | ATTTTTTATA | AAATAAAAGG | GAGAAAATGG | CTATTTAAAT | 1860 |
| ACTAGCCTAT | TTTATTTCAA | TTTTAGCTTA | AAATCAGCCC | CAATTAGCCC | CAATTTCAAA | 1920 |
| TTCAAATGGT | CCAGCCCAAT | TCCTAAATAA | CCCACCCCTA | ACCCGCCCGG | TTTCCCCTTT | 1980 |
| TGATCCAGGC | CGTTGATCAT | TTTGATCAAC | GCCCAGAATT | TCCCCTTTTC | CTTTTTTAAT | 2040 |
| TCCCAAACAC | CCCTAACTCT | ATCCCATTTC | TCACCAACCG | CCACATATGA | ATCCTCTTAT | 2100 |
| CTCTCAAACT | CTCTCGAACC | TTCCCCTAAC | CCTAGCAGCC | TCTCATCATC | CTCACCTCAA | 2160 |
| AACCCACCGG | AATACATGGC | TTCTCAAGCC | GTGGAAACCT | TATACTCACC | TCCCTTTGCT | 2220 |
| CTTACAGTAC | TCGGCCGTCG | ACCGCGGTAC | CCGGG | | | 2255 |